(12) United States Patent
Wan et al.

(10) Patent No.: US 10,285,951 B2
(45) Date of Patent: May 14, 2019

(54) NANOPARTICLE DELIVERY SYSTEMS

(71) Applicant: CELATOR PHARMACEUTICALS, INC., Ewing, NJ (US)

(72) Inventors: Leon Wan, Burnaby (CA); Winnie Lui, Richmond (CA); Paul Tardi, Surrey (CA); Lawrence Mayer, North Vancouver (CA)

(73) Assignee: CELATOR PHARMACEUTICALS, INC., Ewing, NJ (US)

( * ) Notice: Subject to any disclaimer, the term of this patent is extended or adjusted under 35 U.S.C. 154(b) by 0 days.

(21) Appl. No.: 15/744,723

(22) PCT Filed: Jul. 14, 2016

(86) PCT No.: PCT/US2016/042330
§ 371 (c)(1),
(2) Date: Jan. 12, 2018

(87) PCT Pub. No.: WO2017/011685
PCT Pub. Date: Jan. 19, 2017

(65) Prior Publication Data
US 2018/0207104 A1    Jul. 26, 2018

Related U.S. Application Data

(60) Provisional application No. 62/252,396, filed on Nov. 6, 2015, provisional application No. 62/192,973, filed on Jul. 15, 2015.

(51) Int. Cl.
| | | |
|---|---|---|
| *A61K 9/00* | (2006.01) | |
| *A61K 9/51* | (2006.01) | |
| *A61K 47/54* | (2017.01) | |
| *A61K 31/337* | (2006.01) | |
| *A61K 31/517* | (2006.01) | |
| *A61K 31/4184* | (2006.01) | |
| *A61K 31/5377* | (2006.01) | |

(52) U.S. Cl.
CPC .......... *A61K 9/5153* (2013.01); *A61K 9/0019* (2013.01); *A61K 9/5192* (2013.01); *A61K 31/337* (2013.01); *A61K 31/4184* (2013.01); *A61K 31/517* (2013.01); *A61K 31/5377* (2013.01); *A61K 47/554* (2017.08)

(58) Field of Classification Search
CPC .............. A61K 31/337; A61K 31/4184; A61K 31/517; A61K 31/5377; A61K 47/554; A61K 9/0019; A61K 9/5153; A61K 9/5192; B82Y 5/00
See application file for complete search history.

(56) References Cited

U.S. PATENT DOCUMENTS

| | | | |
|---|---|---|---|
| 2003/0118528 A1 | 6/2003 | Walters et al. | |
| 2004/0253228 A1 | 12/2004 | Srivastava | |
| 2010/0331290 A1* | 12/2010 | Ansell .................. | A61K 9/1075 514/172 |
| 2012/0052097 A1* | 3/2012 | Fetzer ..................... | C08L 67/04 424/400 |
| 2013/0337078 A1 | 12/2013 | Mayer et al. | |

FOREIGN PATENT DOCUMENTS

| | | |
|---|---|---|
| WO | WO-2003/028696 | 4/2003 |
| WO | WO 2003028696 A2 * | 4/2003 |
| WO | WO-2006/014626 | 2/2006 |

OTHER PUBLICATIONS

Fisher, "Irinotecan/5-FU/leucovorin, oxaliplatin/5-FU/leucovorin, and oxaliplatin/irinotecan are each effective in the treatment of 5-FU-resistant advanced colorectal cancer," Clin Colorectal Cancer (2001) 1(2):85-86.

Frei et al., "The relationship between high-dose treatment and combination chemotherapy: the concept of summation dose intensity," Clin Cancer Res (1998) 4(9):2027-2037.

International Search Report and Written Opinion for PCT/US16/42330, dated Oct. 4, 2016, 9 pages.

* cited by examiner

*Primary Examiner* — Mark V Stevens
(74) *Attorney, Agent, or Firm* — Morrison & Foerster LLP

(57) ABSTRACT

Nanoparticle compositions described herein comprise combinations of prodrugs of therapeutic agents that achieve enhanced therapeutic effects as compared to those observed when combinations of free forms of these therapeutic agents are administered.

15 Claims, 5 Drawing Sheets

Plasma concentrations of AUY922 and docetaxel in nanoparticle formulation are more than 2-4 orders of magnitude greater than conventional IV formulation

Prodrugs of Docetaxel and AUY922 formulated in PLA-PEG nanoparticles at a 1:2 drug ratio

Note: lowest free drug combination dose using 10 mg/kg docetaxel was excessively toxic (>25% body wt loss)

Combination of Docetaxel and AUY922 formulated in PLA-PEG nanoparticles is more efficacious than the free drug combination Prodrugs of Selumetinib and Ipatasertib formulated in PS:PEG nanoparticles (PS (10k) – PEG (5k)) at a 1:1 or 1:2 drug ratio Prodrugs of Selumetinib and Ipatasertib formulated in PS:PEG nanoparticles
(PS (10k) — PEG (5k)) at a 1:1 or 1:2 drug ratio Combination of Selumetinib and Ipatasertib formulated in PS:PEG nanoparticles
is more efficacious than the free drug combination

NANOPARTICLE DELIVERY SYSTEMS

CROSS-REFERENCE TO RELATED APPLICATIONS

This application is the national phase of PCT application PCT/US2016/042330 having an international filing date of 14 Jul. 2016, which claims benefit of U.S. provisional application No. 62/192,973 filed 15 Jul. 2015, and U.S. provisional application No. 62/252,396 filed 6 Nov. 2015. The contents of the above patent applications are incorporated by reference herein in their entirety.

TECHNICAL FIELD

The invention relates to compositions and methods for improved delivery and reduced toxicity of combinations of therapeutic agents, and to a commercial package or product comprising such a combination.

BACKGROUND ART

The progression of many life-threatening diseases such as cancer, AIDS, infectious diseases, immune disorders and cardiovascular disorders are influenced by multiple molecular mechanisms. Due to this complexity, achieving cures with a single agent has been met with limited success. Thus, combinations of agents have often been used to combat disease, particularly in the treatment of cancers. It appears that there is a strong correlation between the number of agents administered and cure rates for cancers such as acute lymphocytic leukemia and metastatic colorectal cancer (Frei, et al., *Clin. Cancer Res.* (1998) 4:2027-2037; Fisher, M. D., *Clin. Colorectal Cancer* (2001) 1:85-86). In particular, chemotherapeutic agents in combination with potentiating agents, such as heat shock protein inhibitors have been used to successfully treat a number of cancers in the clinic.

Taxanes are a class of widely used anticancer drugs. They are naturally produced by plants belonging to the *Taxus* genus (e.g., Yews). "Taxanes" include paclitaxel, docetaxel, cabazitaxel and other taxane analogs or derivatives thereof.

Potentiating agents as described here are molecularly targeted agents that affect tumorigenesis, often by modulating apoptosis. These agents include heat shock protein (HSP) inhibitors, in particular HSP90 inhibitors (HSPi). HSP90 is a molecular chaperone which stabilizes a variety of proteins required for survival of cancer cells. It is found to be overexpressed in a number of cancer types and therefore inhibition of HSP90 was identified as a potential therapeutic benefit in the treatment of multiple types of malignancies.

Researchers have demonstrated promising improvements in cancer treatment by administering free drug cocktails of a number of taxane/HSP90 inhibitors (HSP90i) combinations. Despite the advantages associated with the use of these free drug cocktails, there are various drawbacks that limit their efficacy including extensive gastrointestinal and ocular toxicity. In addition, administration of the free drug cocktails often results in rapid clearance of one or both of the agents before reaching the target site.

The RAS/RAF/MEK/ERK (Extracellular Signal-Regulated Kinases) pathway is one of the most well-known intracellular pathways and is regulated by receptor tyrosine kinases, cytokines, and heterotrimeric G-protein-coupled receptor. The series of proteins making up this pathway beings with a receptor on the surface of the cell and then transfers information intracellularly through subsequent proteins to the DNA within the nucleus. The pathway includes proteins such as, MAPK (mitogen-activated protein kinases, also called ERK), which communicate by adding phosphate groups to a neighboring protein, and in turn acts as an "on" or "off" switch. When one of the proteins in the pathway is mutated, it can become stuck in the "on" or "off" position—this is a necessary step in the development of many cancers. Components of the MAPK/ERK pathway were discovered when they were found in cancer cells. Numerous drugs that reverse the "on" or "off" switch are being investigated as cancer treatments.

The PI3K/AKT/mTOR or phosphatidylinositol 3-kinase (PI3K)/AKT/mammalian target of rapamycin pathway is another well-known intracellular signaling pathway that is central to cell growth and survival, cell cycle regulation, and programmed cell death. Abnormal activation of this signaling cascade is linked to several disease states, including the majority of human cancers, and therefore many components of the pathway are targets for therapeutic intervention. The PI3K/AKT/mTOR pathway plays a key role in cell proliferation, adhesion, migration, invasion, metabolism, and survival as well as angiogenesis. There are many known factors that enhance this pathway including, EGF, shh, IGF-1, insulin, and CaM; and there are many factors known to inhibit this pathway including PTEN, GSK3B, and HB9.

Researchers have demonstrated promising improvements in cancer treatment by administering free drug cocktails of a number of inhibitors of these pathways. Despite the advantages associated with the use of these free drug cocktails, there are various drawbacks that limit their efficacy including extensive gastrointestinal and ocular toxicity. In addition, administration of the free drug cocktails often results in rapid clearance of one or both of the agents before reaching the target site.

To improve clearance, many anticancer drugs in general have been incorporated into delivery vehicles designed to 'shield' them from mechanisms that would otherwise result in their rapid clearance from the bloodstream. It is well known that nanoparticles have the ability to provide this 'shielding' effect and they are thus often able to extend the half-life of therapeutic agents as well as reduce their toxicity and/or associated drug resistance. Encapsulation into well-designed delivery vehicles can also result in coordinated pharmacokinetics of encapsulated drugs. However, formulation of specific drugs or more than one drug into delivery vehicles has proven to be difficult because the polymer composition of the vehicle often differentially affects the pharmacokinetics of individual drugs. Thus a composition that is suitable for retention and release of one drug may not be suitable for the retention and release of a second drug. Presently, although some active combinations of inhibitors to these pathways are being successfully utilized in clinical trials, a pharmaceutical preparation designed to reduce toxicity and control the pharmacokinetics, and thus tumor delivery, of these drugs has not been described.

PCT publication WO2006/014626 ('626) describes particulate constructs for release of active agents of various kinds. In the nanoparticles of this publication, prodrugs wherein a therapeutic moiety is coupled through a linker to a hydrophobic moiety are assembled into nanoparticles using an amphiphilic stabilizer. The formulations are designed to coordinate release of free drugs from the particles by virtue of hydrolysis of a cleavable bond in the linker that results in the free drug being released from the particles. This is in contrast to the present invention wherein the nanoparticles are designed so as to release the prodrugs in intact form with subsequent hydrolysis in the bloodstream. This subset of the nanoparticles described in the '626 publication results from the appropriate selection of copolymer and the specific ratio of hydrophobic to hydrophilic portion as well as the required range of molecular weights of the hydrophobic portion and the size of the nanoparticles. This results in a different behavior from that focused on in the nanoparticles of the '626 publication.

The present inventors have identified for the first time particular nanoparticle formulations comprising combinations of drugs that result in extended half-lives, reduced toxicity, reduced drug resistance and/or superior efficacy when administered in vivo. Particular illustrative drug combinations include taxane or derivatives thereof and an HSP90 inhibitor and combinations of a RAS/RAF/MEK/ERK inhibitor and a PI3K/AKT/mTOR inhibitor.

DISCLOSURE OF THE INVENTION

It has now been found that by supplying two or more therapeutic agents, each as a prodrug conjugate of a hydrophobic moiety coupled through a linker to said therapeutic agent and encapsulating said prodrugs in nanoparticles of appropriate size by mixing said prodrugs with a copolymer of a hydrophobic portion and a hydrophilic portion of an appropriate ratio and forming said nanoparticles by mixing said mixture with an aqueous phase, compositions are obtained such that a wide variety of therapeutic agents can be provided to subjects, wherein the maximum tolerated dose is increased and plasma concentrations are maintained at a desirable level for long periods of time.

Thus, in one aspect, the invention is directed to a pharmaceutical composition comprising nanoparticles wherein said nanoparticles have an average diameter of less than 80 nm, or preferably 20-80 nm, or even more preferably 40-80 nm, and comprise at least two therapeutic agents, each therapeutic agent coupled through a linker to a hydrophobic moiety to form a prodrug, said nanoparticles also comprising a copolymer of a hydrophobic portion and a hydrophilic portion wherein the weight ratio of the hydrophobic portion to the hydrophilic portion is in the range of 8:5 to 12:5 and wherein the hydrophobic portion has a molecular weight of 8 kD to 15 kD.

The prodrugs may be encapsulated in the same nanoparticle, or in separate nanoparticles. A single composition can be administered as a combination of said agents either encapsulated in the same nanoparticle or in separate nanoparticles or separate compositions of nanoparticles containing each of the prodrugs may be administered. Thus, as used herein, a "composition" includes not only a single composition per se, but also a "set" of compositions wherein the set provides nanoparticles comprising the prodrugs of the therapeutic agents used in combination. Thus, the "set" is simply an alternative way to supply the combination of agents without necessarily premixing individual compositions each including nanoparticles comprising prodrugs of a therapeutic agent. Thus, "a composition" includes this possibility of providing to a subject the combination in separate formulations without mixing them prior to administration. When provided as a "set" of compositions, the administration may be simultaneous or sequential.

Combinations of taxane with heat shock inhibitors or combinations of inhibitors of various kinase pathways are used as examples, but the compositions of the invention can readily include any desired combination of therapeutic agents, and may include more than two therapeutic agents.

In one illustrative embodiment, the invention relates to compositions and methods for administering effective and less-toxic amounts of taxane/HSP90i drug combinations using nanoparticles that are stably associated with at least one taxane and one HSP90i. These compositions allow the two or more agents to be delivered to the disease site in a coordinated fashion, thereby assuring that the agents are present at the disease site at therapeutically active concentrations in order to enhance efficacy. This result will be achieved whether the agents are coencapsulated in nanoparticle or micelle-based delivery vehicles, or are each separately encapsulated in nanoparticle or micelle-based delivery vehicles administered such that therapeutically active concentrations of each are provided at the disease site. The pharmacokinetics (PK) of the composition are controlled by the delivery vehicles themselves such that coordinated delivery is achieved (provided that the PK of the delivery systems are comparable). In one aspect, the taxane and HSP90i are formulated as drug conjugates.

In this specific aspect, the invention is directed to a method to deliver a therapeutically effective amount of a taxane/HSP90i drug combination to a desired target by administering the compositions of the invention.

The invention is also directed to a method to reduce the side effect profile of a taxane/HSP90i drug combination by administering the compositions of the invention. The "reduced side effect profile" may be measured by a reduction in gastrointestinal, ocular and/or other side effects associated with a taxane or taxane/HSP90i drug combination products which are not associated with nanoparticles of the invention. Side effects associated with either free drug cocktails of taxane/HSP90i combinations or nanoparticle-encapsulated taxanes themselves are known by those of ordinary skill and an improved side effect profile using formulations of the invention are readily measured. Thus, provided herein are safer and/or less-toxic compositions comprising a taxane/HSP90i drug combination.

The invention is also directed to a method to reduce drug resistance by administering the taxane/HSP90i drug combination compositions of the invention. Thus, provided herein are compositions comprising a taxane/HSP90i drug combination with reduced drug resistance. Preferably, said drug resistance is taxane-specific drug resistance.

The invention is also directed to a method to deliver a therapeutically effective amount of a taxane/HSP90i drug combination by administering an HSP90i either before, concurrent or after delivery of a taxane stably associated with a delivery vehicle. In preferred aspects, the taxane and/or HSP90i are each conjugated to a hydrophobic moiety.

In another illustrative aspect of the invention compositions and methods for administering effective and less-toxic amounts of combinations of inhibitors of the RAS/RAF/MEK/ERK ("ERK") pathway and/or the PI3K/AKT/mTOR ("AKT") pathway using nanoparticles that are stably associated with at least two of these inhibitors are disclosed. These compositions allow the two or more agents to be delivered to the disease site in a coordinated fashion, thereby assuring that the agents are present at the disease site at therapeutically active concentrations in order to enhance efficacy. This result will be achieved whether the agents are coencapsulated in nanoparticle (including micelle)-based delivery vehicles, or are each separately encapsulated in nanoparticle or micelle-based delivery vehicles administered such that therapeutically active concentrations of each are provided at the disease site. The pharmacokinetics (PK) of the composition are controlled by the delivery vehicles themselves such that coordinated delivery is achieved (provided that the PK of the delivery systems are comparable). In one aspect, the ERK and/or AKT inhibitors are formulated as drug conjugates.

In this illustrative aspect, the invention is directed to a method to deliver a therapeutically effective amount of an ERK/AKT inhibitor drug combination to a desired target by administering the compositions of the invention.

The invention is also directed to a method to reduce the side effect profile of an ERK/AKT inhibitor drug combination by administering the compositions of the invention. The "reduced side effect profile" may be measured by a reduction in papulopustular rash, gastrointestinal, ocular and/or other side effects associated with an ERK/AKT inhibitor drug combination product which is not associated with nanoparticles of the invention. Side effects associated with either free drug cocktails of ERK/AKT inhibitor drug combinations or of each individual inhibitors are known by those of ordinary skill and an improved side effect profile using formulations of the invention is readily measured. Thus, provided herein are safer and/or less toxic compositions comprising an ERK/AKT inhibitor drug combination.

The invention also includes a method to reduce drug resistance by administering the ERK/AKT inhibitor drug combination compositions of the invention. Thus, provided herein are compositions comprising an ERK/AKT inhibitor drug combination with reduced drug resistance.

The invention also includes a method to deliver a therapeutically effective amount of an ERK/AKT inhibitor drug combination by administering an ERK inhibitor either before, concurrent or after delivery of an AKT inhibitor stably associated with a delivery vehicle. In preferred aspects, the ERK inhibitor and/or AKT inhibitor are each conjugated to a hydrophobic moiety.

In some embodiments, an additional therapeutic agent is administered with compositions of the invention.

Some of the combinations of the present invention are useful for treating proliferative diseases. A proliferative disease is mainly a tumor disease (or cancer) (and/or any metastases). The inventive combinations are particularly useful for treating a tumor which is a solid tumor.

MODES OF CARRYING OUT THE INVENTION

Figure 1:
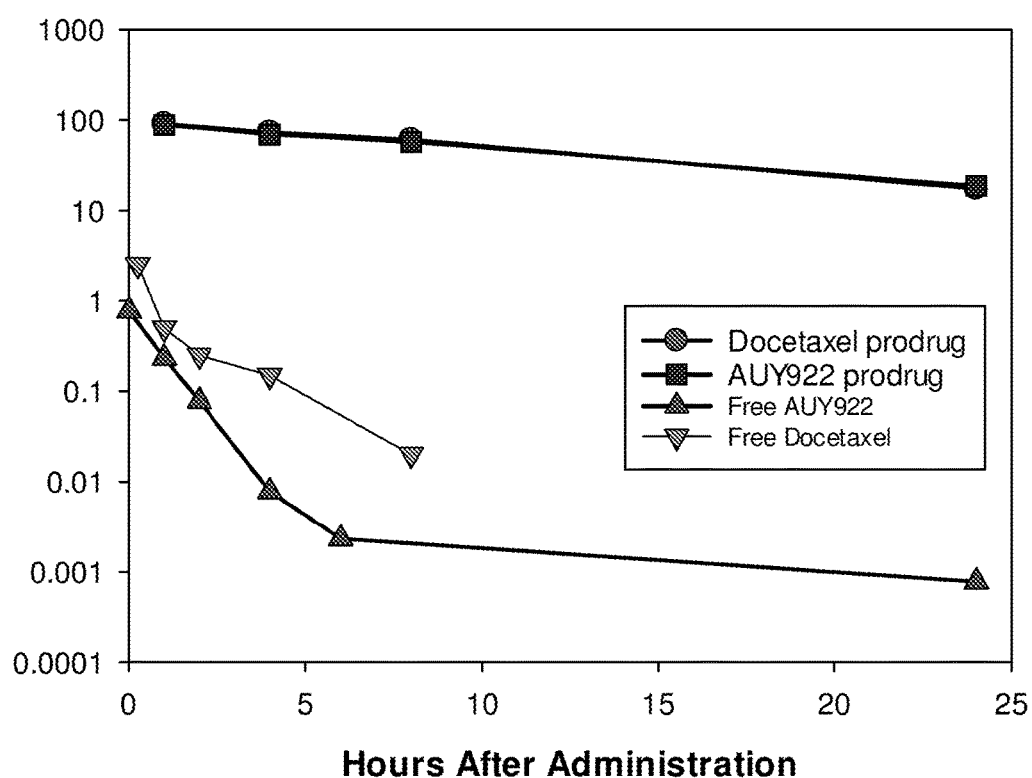
FIG. 1 is a graph of the plasma concentrations (measured as percent of injected dose) of free docetaxel (inverted triangles), free AUY922 (triangles) in comparison to nanoparticle-encapsulated docetaxel (circles) and nanoparticle-encapsulated AUY922 (squares) when administered in vivo.

The preferred drug delivery approach applied here was to combine two well-known concepts, namely the use of prodrugs and the utilization of micellar or nanoparticle delivery vehicles. The goal of most prodrug technologies is typically to make hydrophobic drugs more hydrophilic for increased solubility in an aqueous environment. However, by making them more hydrophobic and consequently more compatible with polymer based delivery systems it is possible to adjust the properties of two disparate drugs such that their effective release rates are matched. Micelles or lipophilic nanoparticle carriers can be used to maintain these prodrugs in aqueous environment since the individual drugs themselves are otherwise insoluble.

Parameters that are likely to affect the in vivo availability of a drug when optimizing the design of such systems include: (1) the plasma elimination of the carrier particle; (2) the partitioning rate of the drug out of the particle; and (3) the hydrolysis rate of the prodrug. In an ideal system the particles remain intact upon i.v. administration, they are cleared relatively slowly from the central blood compartment, and prodrug hydrolysis is relatively rapid, preferably through enzymatic means rather than pH to avoid stability issues in the formulation. The rate limiting process affecting drug availability in the compositions of the present invention is the partitioning rate of the prodrug from the particle to the plasma. A series of prodrugs based on docetaxel and AUY922 and on selumetinib and ipatasertib were investigated in order to validate this general approach to achieving control of the pharmacokinetic behavior of a taxane/HSP90i, or an ERK/AKT inhibitor, drug combination in vivo.

Many attempts have been made to produce functional lipophilic cancer prodrugs to improve the performance of antineoplastic agents or to address formulations issues associated with the drug. These include conjugates with phospholipid, cholesterol, α-bromo fatty acids, oleic acid, fullerene and docosahexaenoic acid. The prodrugs have been formulated in a lipid vehicle, such as liposomes, oil emulsions or micelles. Some of these reports claim improved efficacy over non-prodrug forms in in vivo models. However, in most cases they either provide no information on plasma elimination or present in vivo data covering multiple days after administration which focus on the elimination phase of the drug rather than the distribution phase. Drug elimination information during the first 24 hours after administration is the period of most significant interest from a tumor delivery perspective due to the enhanced permeability and retention (EPR) and decreased clearance by the reticuloendothelial system (RES) as observed with nanoparticulate carriers. The present invention is based on micelles or nanoparticles since these carriers have the ability to provide extended plasma circulation half-lives and maximal drug loading capacity. In addition, micelles have been shown to accumulate in tumors at high levels relative to other tissue.

Turning, then, to the embodiments exemplified herein as typical of drug combinations in general:

Taxanes, particularly paclitaxel and docetaxel are widely used chemotherapeutic agents for treating a range of carcinomas. The paclitaxel clinical material is formulated in Cremophor® EL/ethanol, and is diluted with buffer prior to administration. There are many reports in the literature describing attempts to improve the formulation of paclitaxel using micelles, liposomes or emulsions. In almost all cases however it is clear from the reported pharmacokinetic data that while these carriers formulate paclitaxel, they do not act as true delivery vehicles in vivo since the drug rapidly partitions out of the carrier with a half-life on the order of minutes.

The principles set forth above were applied to formulating HSP90i conjugates for inclusion in nanoparticles, for combination therapy with taxane as well as to formulating AKT and/or ERK inhibitor conjugates for combination therapies. In one illustration, the development of a series of docetaxel and AUY922 prodrugs and associated micellar/nanoparticle formulations is included in the invention. In another illustrative embodiment, the development of selumetinib and ipatasertib prodrugs, for example, and associated micellar/nanoparticle formulations is described.

The invention describes the design of particulate delivery vehicles with prolonged circulation half-lives where the release of both agents is modulated by manipulating the composition of the nanoparticle copolymer and/or the degree of lipid anchor hydrophobicity and/or the lability of the cross-linkers. The pharmacokinetics of the prodrugs in vivo is shown to be highly dependent upon the nature and size of each block of the copolymer. Similarly, the efficacy of the prodrugs in vivo is shown to be dependent on the nature of copolymer, the linkage and/or the relative partitioning rate of the lipid anchor.

In particular, it has been found that over a wide range of therapeutic agent combinations, the formulations are most effective when the size of the nanoparticles is less than 80 nm, or preferably 20-80 nm, or even more preferably 40-80 nm in average diameter and wherein the nanoparticles are formed by assembling into a particle a prodrug wherein a therapeutic agent is coupled through a linker to a hydrophobic moiety and a copolymer comprising a hydrophobic portion and a hydrophilic portion wherein the weight ratio of hydrophobic portion to the hydrophilic portion is in the range of 8:5 to 12:5, preferably 10:5 (or 2:1) and wherein the hydrophobic portion has a molecular weight of 8 kD to 15 kD. This permits ready partition from the particles of the prodrugs in intact form whereupon release of the therapeutic agent itself when the prodrug is liberated to the bloodstream is relatively rapid.

As noted above, two examples employ prodrugs of a taxane and HSP90i or prodrugs of AKT and ERK inhibitors and micellar or nanoparticle delivery vehicles to facilitate pharmacokinetic control. By making these drugs more hydrophobic and consequently more compatible with polymer based delivery systems, the pharmacokinetics of the drug combination compositions can be controlled. It is also possible to adjust the properties of formulations containing additional antineoplastic agents such that their effective release rates in vivo are matched to that of the two drug combinations. Micelles or lipophilic nanoparticle carriers can be used to suspend these prodrugs and other agents in an aqueous environment.

As shown below, long circulating prodrug nanoparticles provide significantly enhanced therapeutic activity over the non-encapsulated drug combinations at the maximum tolerated dose; these types of formulations are therefore advantageous per se.

Thus, exemplary pharmaceutical compositions are those that comprise nanoparticles or micelles formed from a prodrug of a taxane and a prodrug of an HSP90i, or a prodrug of an AKT inhibitor and a prodrug of an ERK inhibitor which prodrugs are conjugates of said agents each coupled to a hydrophobic moiety through a linker wherein said prodrugs are associated with a lipid and/or an amphiphilic stabilizer. In some embodiments, no lipid is required.

The invention also includes methods to administer the above combinations or other drug combinations using the compositions of the invention, to combine the compositions of the invention with formulations of additional antineoplastic agents and administer these and to methods of preparing these compositions and formulations.

The nanoparticle delivery vehicles of the present invention may be used not only in parenteral administration but also in topical, nasal, subcutaneous, intraperitoneal, intramuscular, aerosol or oral delivery or by the application of the delivery vehicle onto or into a natural or synthetic implantable device at or near the target site for therapeutic purposes or medical imaging and the like. Preferably, the nanoparticle delivery vehicles of the invention are used in parenteral administration, most preferably, intravenous administration.

The preferred embodiments herein described are not intended to be exhaustive or to limit the scope of the invention to the precise forms disclosed. They are chosen and described in order best to explain the principles of the invention and its application and practical use to allow others skilled in the art to comprehend its teachings.

Illustrative Drugs

Taxanes

Taxanes are a class of widely used anticancer drugs. They are diterpenes which are naturally produced by plants belonging to the *Taxus* genus (e.g., Yews). "Taxanes" as used herein includes paclitaxel (Taxol™), docetaxel (Taxotere™), cabazitaxel and other taxane analogs or derivatives thereof. Paclitaxel was originally derived from the Yew tree and its analogs include docetaxel and other compounds of similar structure. Taxol™ is a commercially available form of paclitaxel formulated with Cremophor™. More recently another Taxane, cabazitaxel, was approved by the FDA to treat hormone-refractory prostate cancer.

Paclitaxel is a widely used chemotherapeutic agent for treating a range of carcinomas as described above.

Docetaxel is a clinically well-established anti-mitotic anticancer agent that works by interfering with cell division. It is approved by the FDA for treatment of locally advanced or metastatic breast cancer, head and neck cancer, gastric cancer, hormone-refractory prostate cancer and non-small-cell lung cancer. Docetaxel is approximately twice as potent as paclitaxel (due to docetaxel's effect on the centrosome of the mitotic spindle), however it has similar efficacy as paclitaxel which may be due to the fact that docetaxel is prone to cellular drug resistance via a number of different mechanisms.

An exemplified embodiment of a docetaxel prodrug for use of the invention is shown below:

include, but are not limited to, HSP90 inhibitors, HSP70 inhibitors, HSP60 inhibitors. HSP27 inhibitors, and HSP10 inhibitors. Preferably, HSP90 inhibitors (HSP90i) are used.

Among heat shock proteins the focus on HSP90 has increased due to its involvement in several cellular phenomenon and targeting pathways and more importantly in disease progression. HSP90 is a key component of a multi-chaperone complex which is involved in the posttranslational folding of a large number of proteins, many of which play essential roles in tumorigenesis. It regulates the conformation, stability, and function of many critical oncogenic proteins that are essential in maintaining the malignant transformation and in increasing the survival, growth, and invasive potential of cancer cells. HSP90 inhibitors induce degradation of these proteins.

The availability of drugs that can specifically target HSP90 and inhibit its function, resulting in the depletion of client proteins, has made HSP90 a novel and exciting target for cancer therapy. A number of HSP90 inhibitors are currently undergoing clinical trials for a variety of cancers. HSP90 inhibitors include the natural products geldanamycin and radicicol as well as semisynthetic derivatives 17-N-allylamino-17-demethoxygeldanamycin (17AAG). AUY922 (or "NVP-AUY922"; also known as luminespib) is an experimental drug candidate for the treatment of cancer.

Many of these HSP90 inhibitors are highly toxic on their own. For example, geldanamycin is an effective HSP90 inhibitor yet it cannot be used in vivo because of its high toxicity and liver damage ability. The semi-synthetic deriva-

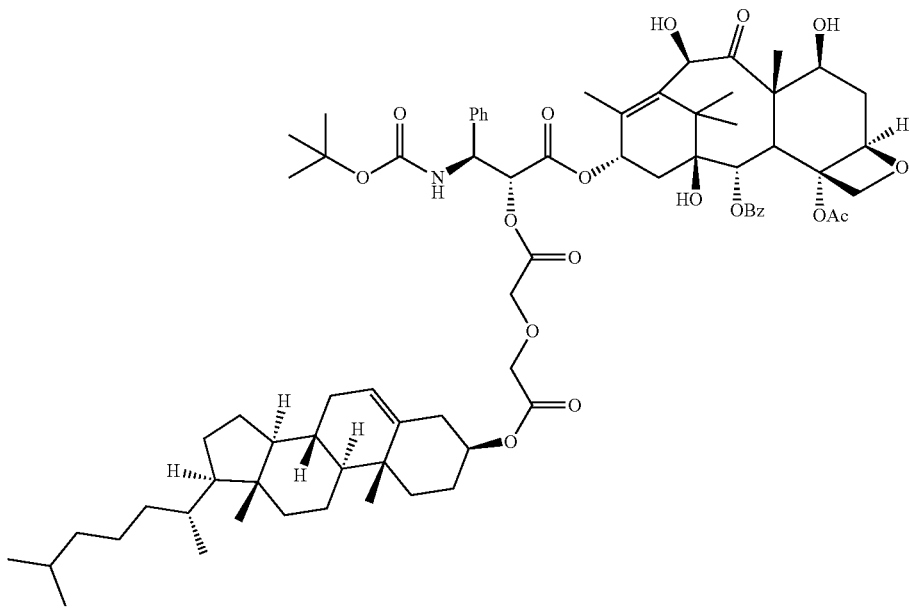

Docetaxel-Diglycolate-Cholesterol

HSP90 Inhibitors

"Potentiating agents" or "molecularly targeted potentiating agents" as described herein refer to compounds targeting tumorigenesis, including modulating apoptotic activity. As used herein, these include, but are not limited to, heat shock protein (HSP) inhibitors. HSP inhibitors of the invention tive 17AAG has somewhat lower toxicity but the same potency as geldanamycin and is currently undergoing clinical trials. AUY922 also on its own is shown to be highly toxic at low doses.

An exemplified embodiment of an HSP90i prodrug for use of the invention is shown below:

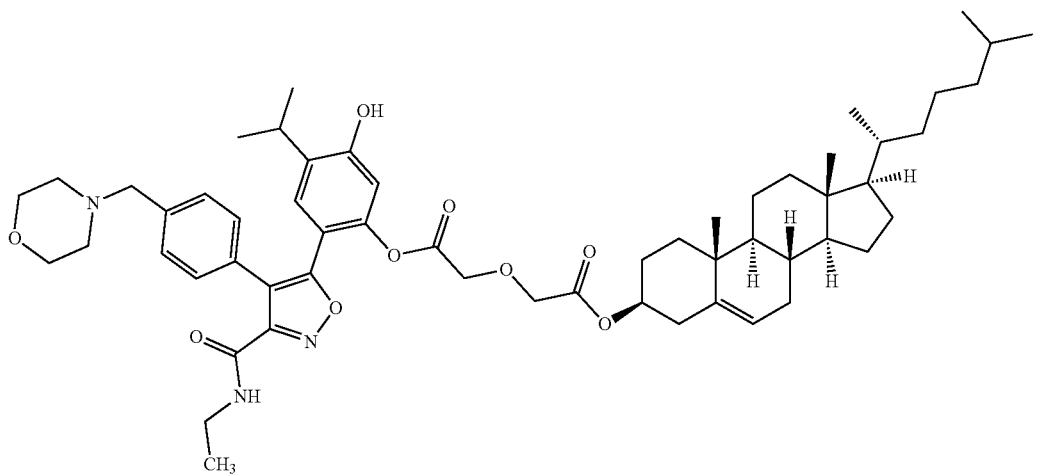

AUY922-Diglycolate-Cholesterol

RAS/RAF/MEK/ERK Inhibitors

An "RAS/RAF/MEK/ERK inhibitor" or "MEK inhibitor" or "ERK inhibitor" as used herein is meant to include any inhibitor with modulates activity at any point along the RAS/RAF/MEK/ERK pathway. Such inhibitors include, for example, selumetinib, GSK1120212, TAK-733, RDEA119, U0126, PD 98059 and D-87503. Many of these inhibitors, such as PD 98059, are highly selective inhibitors of MEK 1 and/or MEK 2. Certain inhibitors act through allosteric inhibition, some are non-ATP competitive inhibitors, and some are reversible inhibitors while others are not.

Selumetinib, also known as AZD6244, is a clinically well-established anticancer agent that works by inhibiting mitogen-activated protein kinase kinase (MEK or MAPK/ERK kinases) 1 and 2.

An exemplified embodiment of a selumetinib prodrug for use of the invention is a selumetinib-cholesterol prodrug linked through either a glycolate or succinate linkage such as that seen below:

PI3K/AKT/mTOR Inhibitors

A "PI3K/AKT/mTOR inhibitor" or "AKT inhibitor" as used herein is meant to include any inhibitor with modulates activity at any point along the PI3K/AKT/mTOR pathway. Such inhibitors include, for example, ipatasertib, wortmannin, GCK690693, perifosine, and SC79.

Some inhibitors, such as wortmannin which is a steroid metabolite, acts by covalent inhibition of PI3K. Others, such as ipatasertib, targets AKT. Similar to above, some act through ATP competitive inhibition while others are non-ATP inhibitors.

Exemplified embodiments of PI3K/AKT/mTOR inhibitor prodrugs for use of the invention are an ipatasertib-cholesterol prodrug linked through either a glycolate or succinate linkage such as that seen below:

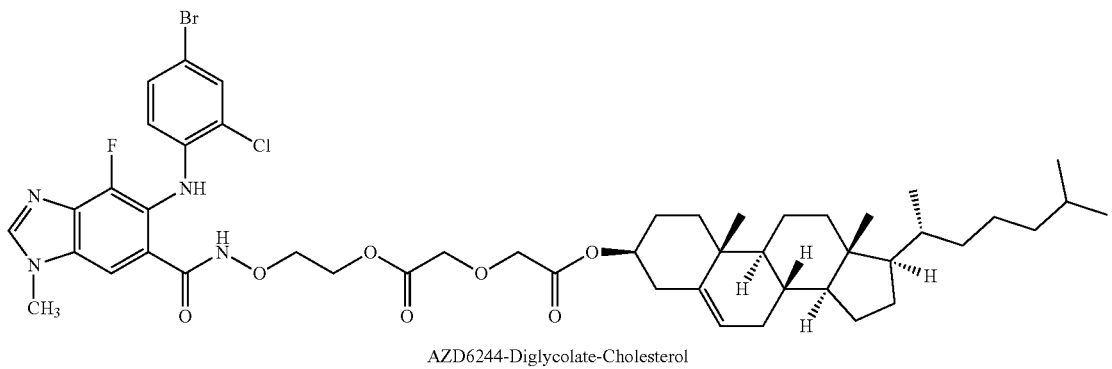

AZD6244-Diglycolate-Cholesterol

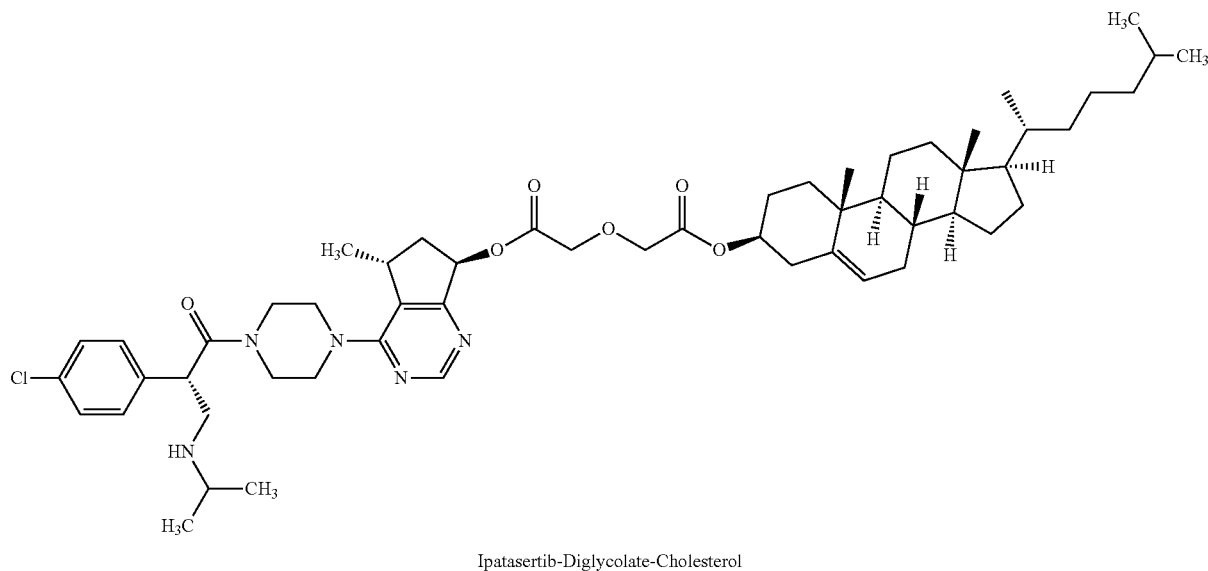

Ipatasertib-Diglycolate-Cholesterol

Preparation of Nanoparticle Delivery Vehicles for Prodrug Combinations

Delivery vehicles may include polymer nanoparticles, polymer microparticles, block copolymer micelles, polymer-lipid hybrid systems, derivatized single chain polymers, lipid micelles, lipoprotein micelles, lipid-stabilized emulsions, cyclodextrins, and the like.

Nanoparticles and microparticles may comprise a concentrated core of drug that is surrounded by a polymeric shell (nanocapsules) or as a solid or a liquid dispersed throughout a polymer matrix (nanospheres). General methods of preparing nanoparticles and microparticles are described by Soppimath, et al. (*J. Control Release* (2001) 70:1-20) the contents of which is incorporated herein. Other polymeric delivery vehicles that may be used include block copolymer micelles that comprise a drug containing a hydrophobic core surrounded by a hydrophilic shell; they are generally utilized as carriers for hydrophobic drugs and can be prepared as found in Allen, et al., *Colloids and Surfaces B: Biointerfaces* (1999) 16:3-27. Polymer-lipid hybrid systems consist of a polymer nanoparticle surrounded by a lipid monolayer. The polymer particle serves as a cargo space for the incorporation of hydrophobic drugs while the lipid monolayer provides a stabilizing interference between the hydrophobic core and the external aqueous environment. Polymers such as polycaprolactone and poly(d,l-lactide) may be used while the lipid monolayer is typically composed of a mixture of lipid. Suitable methods of preparation are similar to those referenced above for polymer nanoparticles. Derivatized single chain polymers are polymers adapted for covalent linkage of a biologically active agent to form a polymer-drug conjugate. Numerous polymers have been proposed for synthesis of polymer-drug conjugates including polyaminoacids, polysaccharides such as dextrin or dextran, and synthetic polymers such as N-(2-hydroxypropyl)methacrylamide (HPMA) copolymer. Suitable methods of preparation are detailed in Veronese and Morpurgo, *IL Farmaco* (1999) 54:497-516 and are incorporated by reference herein.

Micelles are self-assembling particles composed of amphipathic lipids or polymeric components that are utilized for the delivery of sparingly soluble agents present in the hydrophobic core. Various means for the preparation of micellar delivery vehicles are available and may be carried out with ease by one skilled in the art. For instance, lipid micelles may be prepared as described in Perkins, et al., *Int. J. Pharm.* (2000) 200:27-39 (incorporated herein by reference). Lipoprotein micelles can be prepared from natural or artificial lipoproteins including low and high-density lipoproteins and chylomicrons. Lipid-stabilized emulsions are micelles prepared such that they comprise an oil filled core stabilized by an emulsifying component such as a monolayer or bilayer of lipids. The core may comprise fatty acid esters such as triacylglycerol (corn oil). The monolayer or bilayer may comprise a hydrophilic polymer lipid conjugate such as DSPE-PEG. These delivery vehicles may be prepared by homogenization of the oil in the presence of the polymer lipid conjugate. Agents that are incorporated into lipid-stabilized emulsions are generally poorly water-soluble. Synthetic polymer analogues that display properties similar to lipoproteins such as micelles of stearic acid esters or poly(ethylene oxide) block-poly(hydroxyethyl-L-aspartamide) and poly(ethylene oxide)-block-poly(hydroxyhexyl-L-aspartamide) may also be used in the practice of this invention (Lavasanifar, et al., (*J. Biomed. Mater. Res.* (2000) 52:831-835).

In preferred aspects of the invention, nanoparticles are self-assembling. In some embodiments, nanoparticles are self-stabilizing in that they do not require the presence of an additional stabilizer.

Delivery vehicles are thus provided such that consistent delivery of therapeutic concentrations of the above combinations is accomplished. Thus, the plasma concentrations of each agent may be maintained by simple coencapsulation of the agents in the vehicles that comprise the composition or the agents can be encapsulated in separate vehicles if the vehicles control the pharmacokinetics of the composition to maintain the plasma drug concentrations in the same manner.

Prodrug Delivery

The invention provides compositions that show improved delivery characteristics for a therapeutic agent combination wherein said therapeutic agents are formulated as prodrugs. Prodrugs of the invention are made by conjugating the drug to a hydrophobic moiety. Because the pharmacokinetics of the formulation can be controlled by manipulating the nature of the hydrophobic moiety, as well as manipulating the components of the micelles or nanoparticles, particularly the copolymer, desired characteristics of drugs' delivery can be achieved. (For example, the pharmacokinetics of the taxane prodrug can be made to match the pharmacokinetics of the HSP90i prodrug and/or formulations containing other antineoplastic agents, offering the opportunity for an improved system of coordinated drug delivery whereby the concentration of the HSP90i and the taxane delivered to a tumor remains substantially that which is administered. Therefore, a synergistic ratio of the taxane:HSP90i, determined in vitro, can be maintained within a factor of 1.5 or 2 using the improved taxane prodrug formulation in combination with a compatible formulation of the HSP90i. Similar results are obtained for combinations of AKT inhibitors and MEK inhibitors using the same methods and compositions. These formulations are useful in the treatment of cancer and other hyperproliferative indications. The maintenance of the therapeutic agent concentrations can readily be measured by determining the levels of the agents in blood or plasma over time. The coordinated compositions will maintain the administered concentrations as measured in the blood or plasma within the foregoing limits over at least 1 hour or 4 hours or even 24 hours.

A lipid may also be associated with the prodrug(s) in the nanoparticulate compositions of the invention. Such lipids are typically a phospholipid, such as distearoyl phosphatidylcholine, dipalmitoyl phosphatidylcholine, dimyristoyl phosphocholine, and corresponding phosphatidyl ethanols, phosphatidyl inositols, phosphatidyl glycerols, and the like. The fatty acid chains may also be unsaturated and include, for example, oleic and linoleic acids. The fatty acids need not be identical. In addition, the lipid moiety may be a sphingosine such as sphingomyelin or itself a tocopherol ester such as vitamin E succinate or vitamin E adipate.

Prodrugs and Hydrophobic Moieties

The hydrophobic moiety for use in generating prodrugs of the invention may include polymers or natural products. Examples of suitable hydrophobic polymeric moieties include but are not limited to polymers of the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, and vinylimidazole; aminoalkyls including aminoalkylacrylates, aminoalkylmethacrylates, and aminoalkyl(meth)acrylamides; styrenes; cellulose acetate phthalate, cellulose acetate succinate, hydroxypropylmethylcellulose phthalate, and the polymers poly(D,L lactide), poly(D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly (tartronic acid), polyanhydrides, polyphosphazenes, poly (amino acids) and their copolymers (see generally, Ilium, L., Davids, S. S. (eds.) *Polymers in Controlled Drug Delivery*, Wright, Bristol, 1987; Arshady, *J. Control. Release* (1991) 17:1-22; Pitt, *Int. J. Phar.* (1990) 59:173-196; Holland, et al., *J. Control. Release* (1986) 4:155-180); hydrophobic peptide-based polymers and copolymers based on poly(L-amino acids) (Lavasanifar, A., et al., *Adv. Drug Deliver. Rev.* (2002) 54:169-190), poly(ethylene-vinyl acetate) ("EVA") copolymers, silicone rubber, polyethylene, polypropylene, polydienes (polybutadiene, polyisoprene and hydrogenated forms of these polymers), maleic anhydride copolymers of vinyl-methylether and other vinyl ethers, polyamides (nylon 6,6), polyurethane, poly(ester urethanes), poly(ether urethanes), poly(ester-urea). Particularly preferred polymeric hydrophobes include poly(ethylenevinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) For non-biologically related applications particularly preferred polymeric carriers include polystyrene, polyacrylates, and butadienes. The polymers must contain one or more functionizable groups which may be incorporated into the polymer by derivitization or may be inherent in the polymer chemistry. Polymers as hydrophobic moieties should have molecular weights between 800 and 200,000. The preferred range is 1,000 to 10,000 for polymers with mono or divalent functional sites. For polymers with a multiplicity of functional sites for derivation the preferred molecular weight of the polymer per conjugated drug is 1,000 to 10,000.

Natural products with functional groups or groups that can be converted to functional groups for conjugation include: hydrophobic vitamins (for example vitamin E, vitamins K and A), carotenoids and retinols (for example beta carotene, astaxanthin, trans and cis retinal, retinoic acid, folic acid, dihydrofolate, retinyl acetate, retinyl palmitate), cholecalciferol, calcitriol, hydroxycholecalciferol, ergocalciferol, α-tocopherol, α-tocopherol acetate, α-tocopherol nicotinate, and estradiol. Preferred natural products are cholesterol or C22 carbon chains which can be readily obtained.

Depending on the nature of the hydrophobic moiety, it may be able to accommodate more than one, including substantially more than one drug through a multiplicity of linking sites. Polymeric moieties may have as many as 100 sites whereby drugs could be linked. Simpler hydrophobic moieties, such as vitamin E, may provide only one such site. Thus, the number of drugs coupled to a single hydrophobic moiety may be only 1, or may be 2, 5, 10, 25, 100 and more, and all integers in between. For instance, the polymers set forth above can readily be provided with a multiplicity of functional groups for coupling to the drug. Difunctional hydrophobic moieties would include the hydrophobic polymer chains listed above that have two terminal OH, COOH, or $NH_2$ groups. Multifunctional hydrophobic moieties include all of those listed above that have multiple OH, COOH, or $NH_2$ groups on some or all of the monomer units on the polymer backbone. These functional groups are merely illustrative; other moieties which could form functional groups for linking include phenyl substituents, halo groups, and the like. Typically, when the hydrophobic moiety is a hydrophobic polymer, it may have multiple sites for linkage. When the hydrophobic moiety is a relatively small molecule, it will accommodate only the number of linkers for which it has available functional groups.

Amphiphilic Stabilizer Copolymers

The "amphiphilic stabilizer" for use in the invention is preferably a polymeric compound comprising a hydrophilic portion and a hydrophobic portion. More preferably, it is a copolymer of a hydrophilic block coupled with a hydrophobic block. "Hydrophobic" is defined as above. "Hydrophilic" in the context of the present invention refers to moieties that have a solubility in aqueous solution (i.e., a physiological solution as defined above) of at least 1.0 mg/ml. Thus, in the amphiphilic stabilizer, the hydrophobic region, if taken alone, would exhibit a solubility in aqueous medium of less than 0.05 mg/ml and the hydrophilic region, if taken alone, would exhibit a solubility in aqueous medium of more than 1 mg/ml. Examples include copolymers of polyethylene glycol with polylactic acid or poly(lactic-co-glycolic acid) or polystyrene. Typical hydrophobic polymers include polystyrene and hydrophobic derivatives of polymethacrylates as well as polyvinyl derivatives. Typical hydrophilic components include polyethylene glycol and hydrophilic derivatives of hydrophobic polymers, as well as dextran and dextran derivatives and polyamino acids. The list is meant to be exemplary and not exhaustive. Nanoparticles formed by the process of this invention can be formed with graft, block or random amphiphilic copolymers. These copolymers can have a molecular weight between 500 g/mole and 50,000 g/mole or more, or between about 3,000 g/mole to about 25,000 g/mole, or at least 2,000 g/mole.

Examples of suitable hydrophobic blocks in an amphiphilic stabilizer include but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, and vinylimidazole; aminoalkyls including aminoalkylacrylates, aminoalkylmethacrylates, and aminoalkyl(meth)acrylamides; styrenes; cellulose acetate phthalate, cellulose acetate succinate, hydroxypropylmethylcellulose phthalate, poly(D,L lactide), poly (D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) *Polymers in Controlled Drug Delivery*, Wright, Bristol, 1987; Arshady, *J. Control. Release* (1991) 17:1-22; Pitt, *Int. J. Phar*. (1990) 59:173-196; Holland, et al., *J. Control. Release* (1986) 4:155-180); hydrophobic peptide-based polymers and copolymers based on poly(L-amino acids) (Lavasanifar, A., et al., *Adv. Drug Deliver. Rev.* (2002) 54:169-190), poly(ethylene-vinyl acetate) (EVA) copolymers, silicone rubber, polyethylene, polypropylene, polydienes (polybutadiene, polyisoprene and hydrogenated forms of these polymers), maleic anhydride copolymers of vinyl methylether and other vinyl ethers, polyamides (nylon 6,6), polyurethane, poly(ester urethanes), poly(ether urethanes), poly(ester-urea). Particularly preferred polymeric blocks include poly(ethylenevinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, or poly (lactic acid).

Examples of suitable hydrophilic blocks in an amphiphilic stabilizer include but are not limited to the following: polyvinyl alcohol, carboxylic acids including acrylic acid, methacrylic acid, itaconic acid, and maleic acid; polyoxyethylenes or poly ethylene oxide; polyacrylamides and copolymers thereof with dimethylaminoethylmethacrylate, diallyldimethylammonium chloride, vinylbenzylthrimethylammonium chloride, acrylic acid, methacrylic acid, 2-acrylamido-2-methylpropane sulfonic acid and styrene sulfonate, polyvinyl pyrrolidone, starches and starch derivatives, dextran and dextran derivatives; polypeptides, such as polylysines, polyarginines, polyglutamic acids; poly hyaluronic acids, alginic acids, polylactides, polyethyleneimines, polyionenes, polyacrylic acids, and polyiminocarboxylates, gelatin, and unsaturated ethylenic mono or dicarboxylic acids. Polymer stabilizers such as polyvinyl alcohol may also be used on their own.

Preferably the blocks are either diblock or triblock repeats. Preferably, block copolymers for this invention include blocks of polystyrene, polyethylene, polybutyl acrylate, polybutyl methacrylate, polylactic acid, mixtures of lactic and glycolic acid, polycaprolactone, polyacrylic acid, polyoxyethylene and polyacrylamide. A listing of suitable hydrophilic polymers can be found in *Handbook of Water-Soluble Gums and Resins*, R. Davidson, McGraw-Hill (1980).

In graft copolymers, the length of a grafted moiety can vary. Preferably, the grafted segments are alkyl chains of 12 to 32 carbons or equivalent to 6 to 16 ethylene units in length. In addition, the grafting of the polymer backbone can be useful to enhance solvation or nanoparticle stabilization properties. A grafted butyl group on the hydrophobic backbone of a diblock copolymer of a polyethylene and polyethylene glycol should increases the solubility of the polyethylene block. Suitable chemical moieties grafted to the block unit of the copolymer comprise alkyl chains containing species such as amides, imides, phenyl, carboxy, aldehyde or alcohol groups. One example of a commercially available stabilizer is the Hypermer family marketed by Uniqema Co. The amphiphilic stabilizer could also be of the gelatin family such as the gelatins derived from animal or fish collagen.

In some embodiments of the invention, the copolymer is a polylactic acid (PLA)-PEG, polystyrene (PS)-PEG or poly(lactic-co-glycolic acid (PLGA)-PEG copolymer. In some embodiments, the copolymer comprises PLA. PLA-containing nanoparticles may have a longer half-life. In other embodiments, the copolymer is a PLGA-PEG copolymer wherein the PLGA component is 10,000-15,000 Daltons. The copolymer in some embodiments is a PLGA-PEG copolymer wherein the PLGA component is 10,000-15,000 Daltons and the PEG component is approximately 5,000 or less Daltons. In some embodiments, the PLA, PS or PLGA has a molecular weight of 8,000-14,000 Daltons. In certain embodiments of the invention, the ratio of hydrophobic to hydrophilic components of the copolymer will dictate the average size of the nanoparticles. When PEG is used, there is at least about a 2:1 weight:weight ratio of hydrophobic component:PEG, i.e., in the range of 8:5 to 12:5. Preferably the nanoparticles average size is less than 80 nm, e.g. 40 to 80 nm. More preferably the nanoparticles average size is less than 75 nm. In some cases, the nanoparticles average size is from about 20 to 80 nm, about 20 to 75 nm or about 50 to 75 nm. In some embodiments, the ratio of taxane prodrug: HSP90i prodrug:copolymer is 1:1:4 to 1:1:16, or 1:1:4 to 1:1:12 and the ratio of AKT inhibitor prodrug:ERK inhibitor prodrug:copolymer is 1:1:4 to 1:1:16, or 1:1:4 to 1:1:12.

When making nanoparticles of the invention it is critical to ensure that the prodrug is adequately dissolved in solvent prior to mixing. In certain embodiments, the nature of the solvent will alter the average size of the nanoparticles. For copolymers with PLGA, acetonitrile is the preferred solvent. For copolymers with PLA, dimethylformamide (DMF) is the preferred solvent. In some embodiments, the temperature of manufacturing nanoparticles of the invention does not alter the average size of the nanoparticles. In some embodiments, nanoparticles of the invention are stable at 4° C., −20° C. and as low as −80° C. In some embodiments, nanoparticles of the invention maintain their average size and drug payload (measured as a particle size change of less than 10 nm with more than 90% drug payload retained) after at least one freeze/thaw round.

Administering Compositions of the Invention In Vivo

Compositions of the present invention may be administered to warm-blooded animals, including humans as well as to domestic and/or avian species. In addition to pharmaceutical compositions, suitable formulations for veterinary use may be prepared and administered in a manner suitable to the subject. Preferred veterinary subjects include mammalian species, for example, non-human primates, dogs, cats, cattle, horses, sheep, and domesticated fowl. Subjects may also include laboratory animals, for example, in particular, rats, rabbits, mice, and guinea pigs. For treatment of human ailments, a qualified physician will determine how the compositions of the present invention should be utilized with respect to dose, schedule and route of administration using established protocols. Such applications may also utilize dose escalation should agents encapsulated in delivery vehicle compositions of the present invention exhibit reduced toxicity to healthy tissues of the subject.

Preferably, the pharmaceutical compositions of the present invention are administered parenterally, i.e., intraarterially, intravenously, intraperitoneally, subcutaneously, or intramuscularly. More preferably, the pharmaceutical compositions are administered intravenously or intraperitoneally by a bolus injection. For example, see Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578, incorporated by reference.

In other methods, the pharmaceutical or cosmetic preparations of the present invention can be contacted with the target tissue by direct application of the preparation to the tissue. The application may be made by topical, "open" or "closed" procedures. By "topical", it is meant the direct application of the multi-drug preparation to a tissue exposed to the environment, such as the skin, oropharynx, external auditory canal, and the like. "Open" procedures are those procedures that include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Alternatively, the preparations may be administered through endoscopic devices.

Pharmaceutical compositions comprising delivery vehicles of the invention are prepared according to standard techniques and may comprise water, buffered water, 0.9% saline, 0.3% glycine, 5% dextrose and the like, including glycoproteins for enhanced stability, such as albumin, lipoprotein, globulin, and the like. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and the like.

The concentration of delivery vehicles in the pharmaceutical formulations can vary widely, such as from less than about 0.05%, usually at or at least about 2-5% to as much as 10 to 30% by weight and will be selected primarily by fluid volumes, viscosities, and the like, in accordance with the particular mode of administration selected. For example, the concentration may be increased to lower the fluid load associated with treatment. Alternatively, delivery vehicles composed of irritating lipids may be diluted to low concentrations to lessen inflammation at the site of administration. For diagnosis, the amount of delivery vehicles administered will depend upon the particular label used, the disease state being diagnosed and the judgment of the clinician.

EXAMPLES

The following examples are offered to illustrate but not to limit the invention.

Example 1

Prodrug Synthesis for Taxane/HSP90 Inhibitor Nanoparticle Combinations

Synthesis of Prodrugs

Docetaxel derivatives were prepared selectively by exploiting the difference in reaction rates between the docetaxel hydroxyl groups. Under the reaction conditions used here, the majority of docetaxel was consumed before significant levels of the diacyl product were generated, as monitored by TLC. Column chromatography was used to remove unreacted docetaxel, the diacyl product and other impurities in the crude reaction mixture. Purity and identity of the final products were confirmed by HPLC and nmR analysis, respectively.

For synthesis of the docetaxel conjugates, docetaxel (1 equivalent), a lipid acid (2 equivalents) and 4-N,N-dimethylaminopyridine (3 equivalents) were dissolved in alcohol free chloroform. Diisopropylcarbodiimide (1.3 equiv.) was then added and the solution stirred at room temperature. The reaction was monitored by TLC until most of the docetaxel had been consumed (typically 2-4 hours). The reaction mixture was then washed with dilute hydrochloric acid and dried over anhydrous magnesium sulfate. After removal of solvent the crude product was passed down a silica gel column using a methanol/methylene chloride gradient. The purified prodrug was lyophilized from benzene and stored at room temperature.

For synthesis of the AUY922 conjugate: see schematic below for AUY922-cholesterol:

Scheme 1:

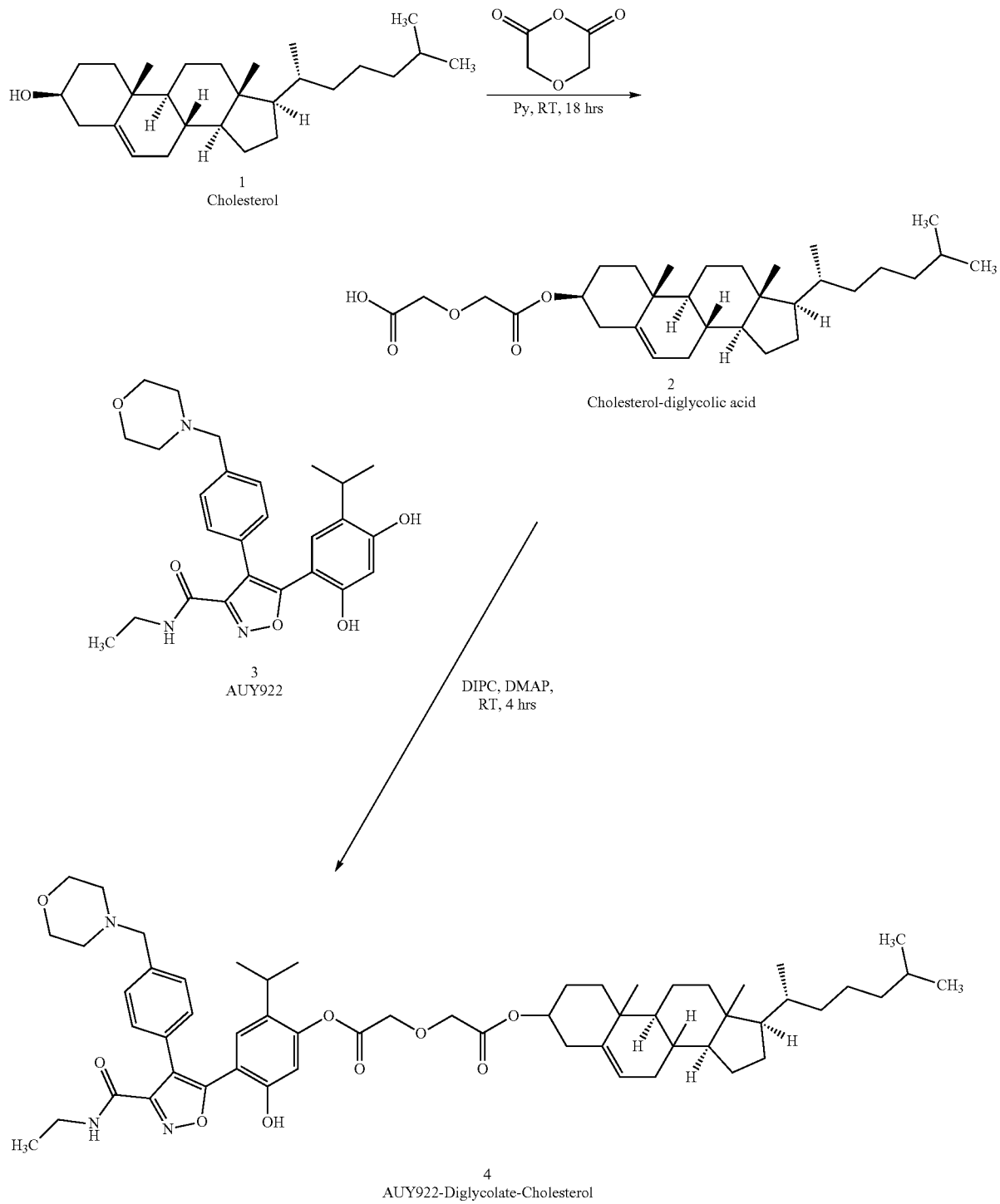

Step 1:

Synthesis of cholesterol-diglycolic acid: diglycolic anhydride (10.20 g, 87.88 mmol) was added in small portions over a period of 15 minutes to a stirred and clear solution of cholesterol (1, 20.0 g, 51.70 mmol) in pyridine (100 mL) at room temperature under nitrogen atmosphere. The resulting pale yellow solution was stirred for 18 hours at room temperature. Reaction was monitored by TLC using 5% methanol in dichloromethane as eluent and spray dried with p-anisaldehyde staining solution. After complete consumption of cholesterol, the mixture was concentrated on a rotary evaporator under vacuum at 30° C. to distill out most of the pyridine and the resulting syrup was poured over ice-cold water (500 mL) under rigorous stirring. The contents were stirred for 10 minutes to quench and solubilize excess diglycolic anhydride. The solid separated was collected via vacuum filtration. It was then suspended in 10% aqueous HCl solution and stirred rigorously for 10 minutes with occasional sonication. Filtered and washed with cold water to a neutral pH and dried in a vacuum oven at 30° C. for 6 hours to get free flowing powder. It was then dissolved in dichloromethane (15 mL) and loaded on a silica gel (1500 g) column. Eluted with a gradient of 1-3% methanol in dichloromethane and the fractions containing product were collected and concentrated. The resulting solid was co-evaporated with dichloromethane (3×10 mL) and dried under high vacuum overnight to get cholesterol-diglycolic acid (22.8 g) as a white powder in 87% yield. $^1$H nmR (400 MHz, CDCl$_3$): δ 5.46-5.40 (m, 1H), 4.83-4.72 (m, 1H), 4.28 (s, 2H), 4.25 (s, 2H), 2.43-2.35 (m, 2H), 2.08-1.96 (m, 2H), 1.95-1.80 (m, 4H), 1.70-1.45 (m, 6H), 1.45-1.25 (m, 4H), 1.25-1.10 (m, 6H), 1.09-0.96 (m, 3H), 0.94 (d, J=8 Hz, 3H), 0.90 (d, J=4 Hz, 3H), 0.88 (d, J=4 Hz, 3H), 0.70 (s, 3H) ppm. ESI-MS Data: m/z=525.35 [M+Na].

Step 2:

Synthesis of AUY922-diglycolate-cholesterol: Weighed amounts of cholesterol-diglycolic acid (2, 12.0 g, 23.86 mmol), AUY922 (3, 10.0 g, 21.48 mmol) and N,N-dimethylamino pyridine (3.0 g, 24.55 mmol) were stored under high vacuum for 10 minutes and purged with nitrogen. The contents were then dissolved in anhydrous dichloromethane (200 mL) and stirred at 19° C. under nitrogen atmosphere. To this, a solution diisopropyl carbodiimide (6.0 mL, 38.98 mmol) in dichloromethane (25 mL) was introduced over a period of 15 minutes and the mixture was stirred at 19° C. for 4 hours. Reaction was monitored by TLC using 10% methanol in dichloromethane as eluent and spray dried with p-anisaldehyde staining solution or observed under UV light. After complete consumption of cholesterol-diglycolic acid (2), the resultant hazy solution was cooled to −15° C. and the solid separated was removed by filtration through a cotton pad and filtrates from this batch and recycled AUY922 (2.0 g) batch were combined and concentrated to a thick solution.

Purification:

The thick solution was loaded on a pre-packed silica gel column in dichloromethane (1500 g). Eluted with 1-5% methanol in dichloromethane. Fractions containing major product were concentrated to get pale yellow solid foam (11.50 g). The solid foam was subjected to another silica gel chromatographic purification by loading on a pre-packed silica gel column in dichloromethane (1500 g). The column was eluted with an isocratic eluent system with a solvent ratio of 3/0.5/96.5 methanol/isopropanol/dichloromethane. This process of purification on silica gel column was repeated until >95% purity by HPLC and nmR was achieved. Alternatively, the product was passed through a reverse phase column (RP, C-18) in neat methanol with a loading ratio of 0.5 g per 240 g of C-18 column. Pure product fractions were collected and concentrated. Dried in vacuum oven for 18 hours to get pure AUY922-diglycolate-cholesterol (4) as off-white powder (4.95 g, 24% yield, HPLC purity 98% at 230 nm). $^1$H nmR (600 MHz, DMSO-d$_6$): δ 10.42 (s, 1H), 8.86 (t, J=4 Hz, 1H), 7.23 (ABq, J=8, 40 Hz, 4H), 6.96 (s, 1H), 6.72 (s, 1H), 5.37 (bs, 1H), 4.58-4.53 (m, 1H), 4.29 (s, 2H), 4.17 (s, 2H), 3.60-3.53 (m, 4H), 2.08 (bs, 2H), 3.33 (bs, 2H), 3.26-3.17 (m, 2H), 3.12-3.00 (m, 1H), 2.40-2.30 (m, 6H), 2.05-1.90 (m, 2H), 1.90-1.75 (m, 3H), 1.65-1.45 (m, 5H), 1.44-1.20 (m, 6H), 1.19-0.95 (m, 17H), 0.94-0.91 (m, 9H), 0.88 (d, J=4 Hz, 3H), 0.70 (s, 3H) ppm. ESI-MS Data: m/z=950.59 [M+H].

The prepared compounds are: docetaxel-cholesterol and AUY922-cholesterol each linked through a glycolate linker.

Example 2

Prodrug Nanoparticle Formulation of Docetaxel and AUY922 Dramatically Increases Plasma Drug Concentrations The taxane and AUY922 prodrugs described in Example 1 were combined to generate nanoparticles of the invention. A number of different nanoparticles were formed including those comprising PLA-PEG or PLGA-PEG copolymers at the following molecular weights ("K" refers to thousands):

PLA(10K)-PEG(5K); PLA(8K)-PEG(5K); PLA(13K)-PEG(2K); PLA(14K)-PEG(4K); PLA(11K)-PEG(5K); PLGA(10K)-PEG(5K); PLGA(10K)-PEG(2K); and PLGA (15K)-PEG(5K).

Nanoparticles comprising PLA-PEG which showed optimal size and stability at a 2:1 ratio, i.e., PLA(10K)-PEG (5K), were formed with docetaxel-cholesterol and AUY922-cholesterol prodrugs for use in these pharmacokinetic studies.

As shown in FIG. 1, the percent injected dose of each prodrug remained at near 50% for up to 12 hours, and 20% for up to 24 hours in comparison to free docetaxel and free AUY922 which have been shown in the art to be cleared quite rapidly.

Example 3

Improved Tolerability of Docetaxel:AUY-922 Combination Formulated into Nanoparticles vs Free Drug Combination The relative tolerability of docetaxel and AUY922 administered as a combination in the form of the prodrugs of Example 1 and in nanoparticles formed with PLA(10K)-PEG(5K) copolymers in viva was compared to the maximum tolerated dose (MTD) of each of the free drugs administered individually.

Figure 2:
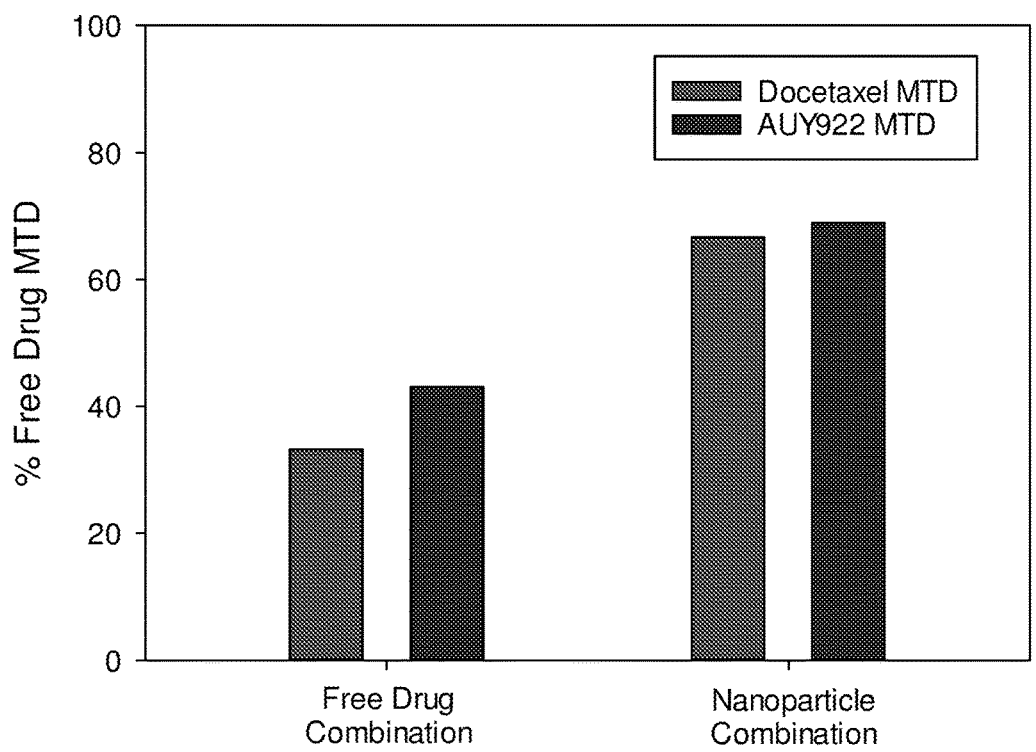
FIG. 2 is a graph of the relative tolerability of docetaxel and AUY922 administered as a nanoparticle combination compared to the maximum tolerated dose (MTD) of the free drugs administered individually and in combination.

As shown in FIG. 2, the combination of docetaxel and AUY922 was significantly more tolerable when formulated into nanoparticles of the invention in comparison to the tolerability of the free drugs administered separately.

Example 4

Efficacy of Docetaxel and an HSP90 Inhibitor in the ST996 PDX Tumor Model (Categorized as Taxane Resistant)

In order to determine whether prodrug combinations of docetaxel and AUY922 were more tolerable and/or efficacious when combined in nanoparticles of Example 3 as compared to administration when un-encapsulated, nanoparticle combinations of the invention were administered to mice expressing a taxane-resistant ST996 PDX tumor model.

Figure 3:
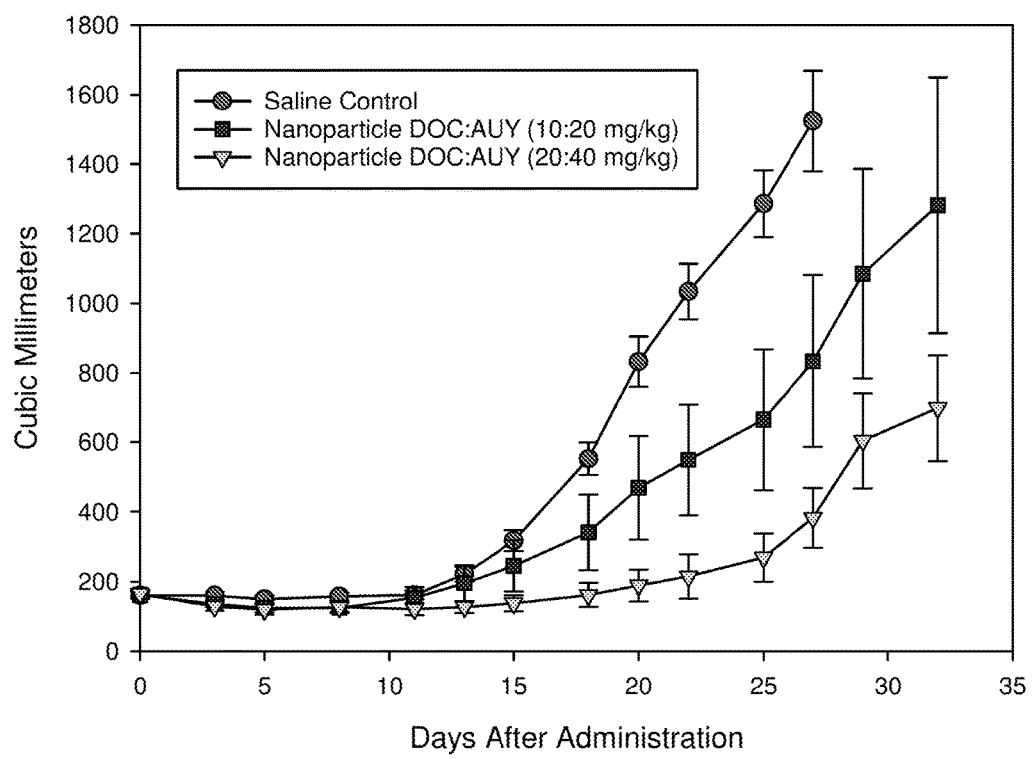
FIG. 3 is a graph of the efficacy of a combination of docetaxel and AUY922 coencapsulated in nanoparticles of the invention and administered at a 1:2 docetaxel:AUY922 wt/wt ratio at either a 10 mg docetaxel dose (squares) or a 20 mg docetaxel dose (triangles) when administered to mice bearing the ST996 PDX tumor model which is characterized as being taxane-resistant.

As shown in FIG. 3, the combination of docetaxel and AUY922 was more tolerable/less toxic when formulated into nanoparticles of Example 3 in comparison to administration of these drugs when un-encapsulated.

Figure 4:
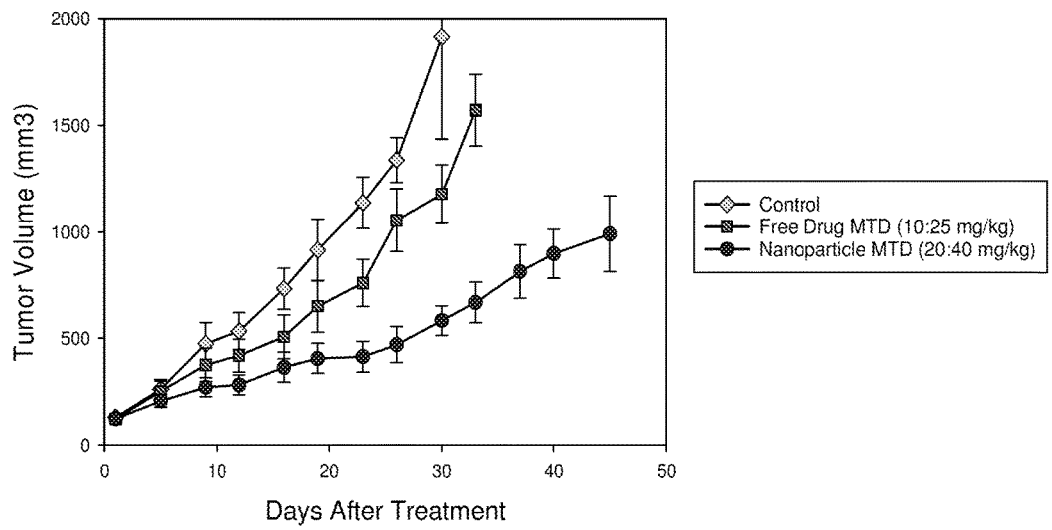
FIG. 4 is a graph of the efficacy of a combination of docetaxel and AUY922 coencapsulated in nanoparticles of the invention in comparison to the free drug combination at its MTD when administered to mice bearing the HCT15 tumor model which is characterized as being taxane-resistant.

Similar results were achieved in a second taxane-resistant tumor model, HCT15 seen in FIG. 4, which also shows that the combination of docetaxel and AUY922 was more efficacious when formulated into nanoparticles of Example 3 in comparison to administration of these two free drugs at their MTD.

Example 5

Efficacy of Selumetinib and Ipatasertib in the HCT116 Human Colon Cancer Tumor Model In order to determine whether combinations of selumetinib and ipatasertib prodrugs were more tolerable and/or efficacious when combined in nanoparticles as compared to administration when un-encapsulated, nanoparticle combinations of the invention were administered to mice bearing the HCT116 tumor model. The nanoparticles comprise polystyrene-PEG, PS (20 k)-PEG (5 k), and the prodrugs described above wherein these agents are coupled to cholesterol through a diglycolate linker.

Figure 5A:
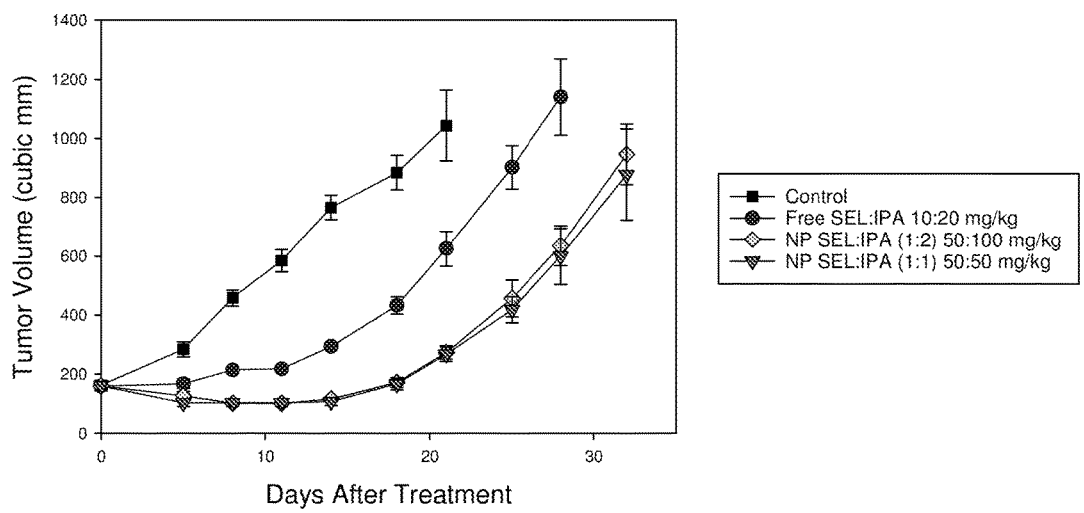
FIG. 5A is a graph of the efficacy of a combination of selumetinib and ipatasertib coencapsulated in nanoparticles of the invention in comparison to the free drug combination (circles) when administered to mice bearing the HCT116 tumor model. Selumetinib is administered as a 10 mg/kg dose in the free drug combination and a 50 mg/kg dose when encapsulated. Ipatasertib is administered at a 20 mg/kg dose in the free drug combination and a 50 mg/kg dose (inverted triangles) or 100 mg/kg dose (diamonds) when coencapsulated in nanoparticles of the invention.

As shown in FIG. 5A, the combination of selumetinib and ipatasertib at two different drug:drug ratios was more tolerable/less toxic when formulated into these nanoparticles in comparison to administration of these drugs when un-encapsulated.

Figure 5B:
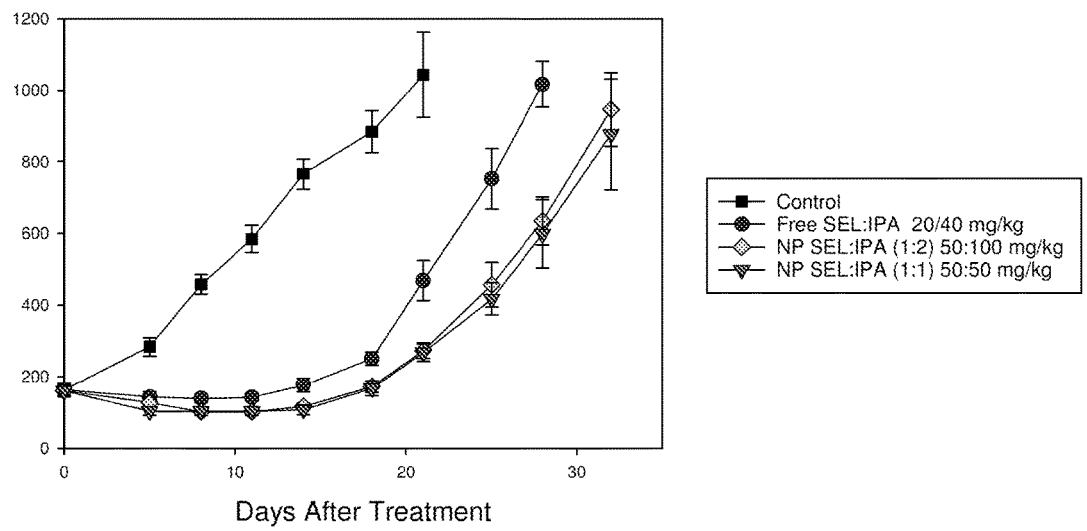
FIG. 5B is a graph of the efficacy of a combination of selumetinib and ipatasertib coencapsulated in nanoparticles of the invention in comparison to the free drug combination (circles) when administered to mice bearing the HCT116 tumor model. Selumetinib is administered as a 20 mg/kg dose in the free drug combination and a 50 mg/kg dose when encapsulated. Ipatasertib is administered at a 40 mg dose in the free drug combination and a 50 mg/kg dose (inverted triangles) or 100 mg/kg dose (diamonds) when coencapsulated in nanoparticles of the invention.

Similar results were achieved when the dose of selumetinib and ipatasertib in the free drug cocktail was doubled (see FIG. 5B).

Example 6

Efficacy of Selumetinib and Ipatasertib in the HCT-15 Multi-Drug Resistant Colon Cancer Model In order to determine whether prodrug combinations of selumetinib and ipatasertib were more tolerable and/or efficacious when combined in nanoparticles of Example 5 as compared to administration when un-encapsulated, similar studies as in Example 5 were repeated in a multi-drug resistant HCT-15 tumor model.

Figure 6:
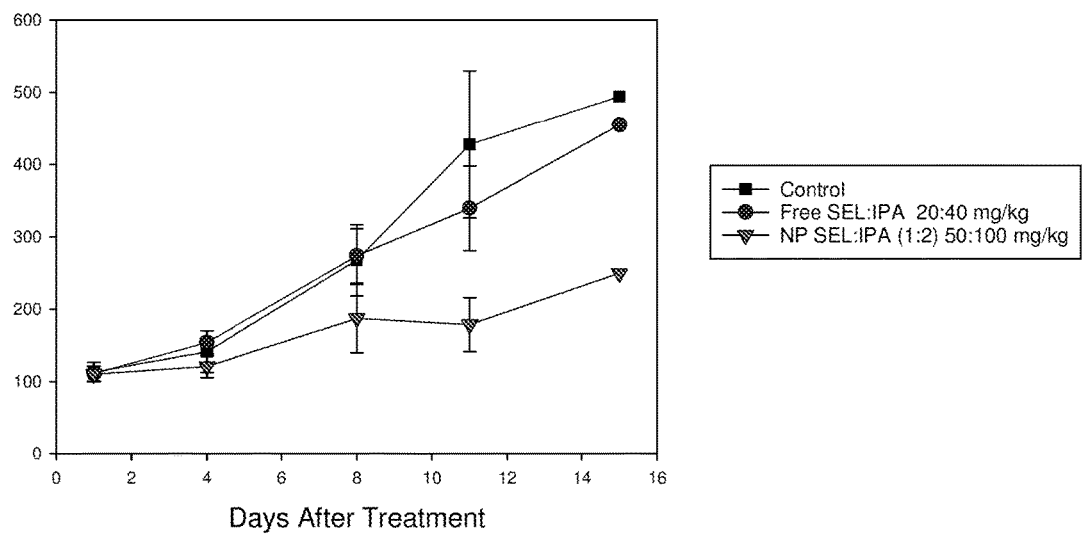
FIG. 6 is a graph of the efficacy of a combination of selumetinib and ipatasertib coencapsulated in nanoparticles of the invention in comparison to the free drug combination (circles) when administered to mice bearing the HCT-15 tumor model. Selumetinib is administered as a 20 mg/kg dose in the free drug combination and a 50 mg/kg dose when encapsulated. Ipatasertib is administered at a 40 mg/kg dose in the free drug combination and a 100 mg/kg dose when coencapsulated in nanoparticles of the invention.

As shown in FIG. 6, the combination of selumetinib and ipatasertib at the 1:2 drug:drug ratio was more tolerable/less toxic when formulated into nanoparticles of Example 5 in comparison to administration of these drugs at a 1:2 ratio when un-encapsulated.

The invention claimed is:

1. A pharmaceutical composition comprising nanoparticles, wherein said nanoparticles have an average diameter of less than 80 nm and said nanoparticles comprise:
   a) at least two different therapeutic agents, each said therapeutic agent couple through a linker to cholesterol or to a hydrophobic natural product to form a prodrug, and
   b) an amphiphilic copolymer stabilizer comprising a hydrophobic portion and a hydrophilic portion wherein the weight ratio of the hydrophobic portion to the hydrophilic portion is in the range of 8:5 to 12:5 and wherein the hydrophobic portion has a molecular weight of 8 kD to 15 kD and wherein the prodrugs of said two different therapeutic agents are contained in the same nanoparticles or are contained in separate nanoparticles.

2. The composition of claim 1 wherein said amphiphilic stabilizer is a diblock copolymer.

3. The composition of claim 1 wherein in said amphiphilic stabilizer, the hydrophobic portion comprises polylactic acid (PLA) or poly(lactic-co-glycolic acid) (PLGA) and the hydrophilic portion comprises polyethylene glycol (PEG).

4. The composition of claim 1 wherein said prodrugs of said at least two therapeutic agents are included in the same nanoparticle.

5. The composition of claim 1 wherein one therapeutic agent is a taxane and the other therapeutic agent is an HSP inhibitor or wherein one therapeutic agent is a PI3K/AKT/mTOR inhibitor and the other therapeutic agent is an RAS/RAF/MEK/ERK inhibitor.

6. The composition of claim 1 wherein in each of said prodrugs the hydrophobic moiety is cholesterol and/or the linker is diglycolic acid.

7. The composition of claim 1 wherein said nanoparticles are formed by mixing an aqueous phase and an organic phase, said organic phase comprising said copolymer and said prodrug.

8. The composition of claim 7 wherein said mixing is conducted by rapid mixing of jet streams one of which comprises the aqueous phase and the other of which comprises the organic phase.

9. The composition of claim 1 wherein said nanoparticles have an average diameter of 20-80 nm.

10. The composition of claim 1 which further comprises a third therapeutic agent.

11. The composition of claim 10 wherein said third therapeutic agent is supplied as a prodrug and encapsulated in said nanoparticles.

12. A method to administer a combination of two or more therapeutic agents which method comprises administering to a subject the composition of claim 1.

13. The method of claim 12 wherein said administering is by parenteral administration.

14. The method of claim 13 wherein the subject is human or non-human mammal or avian.

15. A method to prepare the composition of claim 1 which method comprises rapidly mixing an aqueous phase with an organic phase comprising said copolymer and said prodrug.

* * * * *

UNITED STATES PATENT AND TRADEMARK OFFICE
CERTIFICATE OF CORRECTION

PATENT NO. : 10,285,951 B2  
APPLICATION NO. : 15/744723  
DATED : May 14, 2019  
INVENTOR(S) : Leon Wan Page 1 of 1

It is certified that error appears in the above-identified patent and that said Letters Patent is hereby corrected as shown below:

In the Claims

At Column 25, Claim number 1, Line number 45: please replace "couple" with --coupled--

At Column 25, Claim number 1, Line number 46: please replace "or to a hydrophobic natural product" with --or to another hydrophobic natural product--

At Column 26, Claim number 1, Line number 5: please replace "nanoparticles" with --nanoparticle--

Signed and Sealed this  
Twenty-ninth Day of September, 2020

Andrei Iancu  
*Director of the United States Patent and Trademark Office*